United States Patent [19]
Shiraishi et al.

[11] Patent Number: 5,270,162
[45] Date of Patent: Dec. 14, 1993

[54] AUTORADIOGRAPHIC GENE-SCREENING METHOD

[75] Inventors: Hisashi Shiraishi, Minami-ashigara; Junji Miyahara; Hisatoyo Kato, both of Kaisei, all of Japan

[73] Assignee: Fuji Photo Film Co., Ltd., Kanagawa, Japan

[21] Appl. No.: 735,675

[22] Filed: Jul. 29, 1991

Related U.S. Application Data

[63] Continuation of Ser. No. 431,701, Oct. 20, 1989, abandoned, which is a continuation of Ser. No. 219,849, Jul. 11, 1988, abandoned, which is a continuation of Ser. No. 17,088, Feb. 20, 1987, abandoned, which is a continuation of Ser. No. 651,279, Sep. 17, 1984, abandoned.

[30] Foreign Application Priority Data

Sep. 19, 1983 [JP] Japan ................................. 58-173393

[51] Int. Cl.$^5$ ................ C12Q 1/68; C12Q 1/70; G03C 5/16; G01N 27/26
[52] U.S. Cl. .............................. 435/6; 435/5; 204/182.8; 250/581
[58] Field of Search .............................. 435/6

[56] References Cited

U.S. PATENT DOCUMENTS 4,239,968 12/1980 Kotera et al. ................ 252/301.4 X

FOREIGN PATENT DOCUMENTS 0056638 7/1982 European Pat. Off. .
0113672 7/1984 European Pat. Off. ........ 250/327.2

OTHER PUBLICATIONS

Southern, E. M. J. Mol. Biol. 98 (1975):503–17.
Alwine, J. C. et al, Proc. Natl. Acad. Sci. USA 74(1977):5350–4.
Thomas, P. S. Proc. Natl. Acad. Sci. USA 77(1980):5201–5205.

Primary Examiner—Margaret Moskowitz
Assistant Examiner—Scott A. Chambers
Attorney, Agent, or Firm—Sixbey, Friedman, Leedom & Ferguson

[57] ABSTRACT

An autoradiographic gene-screening method employing a hybridization process, which comprises:
(1) a step of transferring at least a portion of nucleic acids, fragments thereof or derivatives thereof resolved on a medium onto a transfer support to fix them thereonto;
(2) a step of hybridizing the nucleic acids, fragments thereof or derivatives thereof fixed onto said transfer support with radioactively labeled probes; and
(3) a step of obtaining locational information on the radioactively labeled substances on said transfer support, which comprises placing said transfer support having been subjected to the hybridization and a stimulable phosphor sheet in layers for a given period of time to cause said sheet to absorb at least a portion of radiation energy emitted by the radioactively labeled substances on said transfer support, exciting said stimulable phosphor sheet with an electromagnetic wave to release the radiation energy stored in said sheet as stimulated emission, and detecting the stimulated emission.

8 Claims, 2 Drawing Sheets

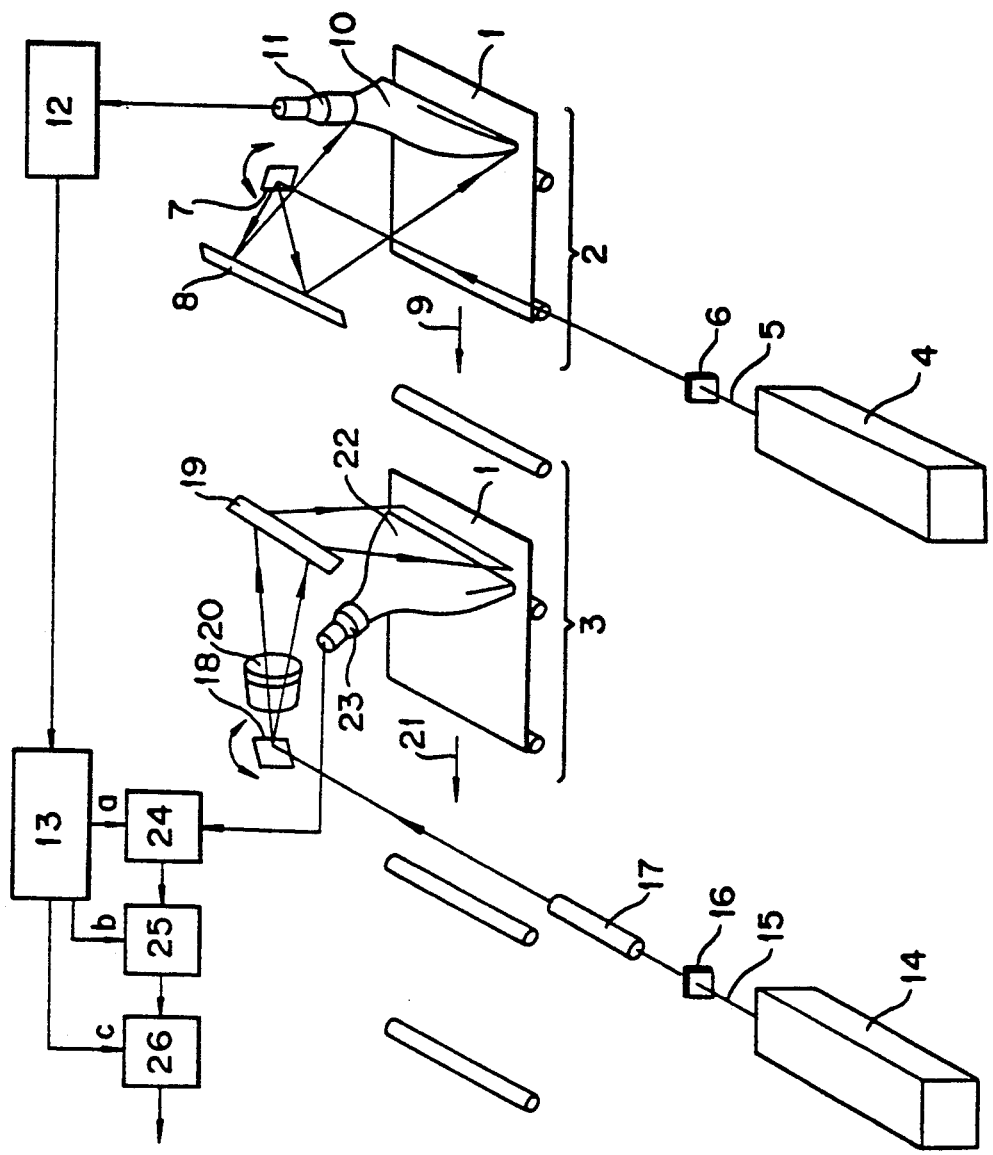

AUTORADIOGRAPHIC GENE-SCREENING METHOD

This application is a continuation of Ser. No. 07/431,701, filed Oct. 20, 1989, now abandoned, which was a continuation of Ser. No. 07/219,849, filed Jul. 11, 1988, abandoned, which was a continuation of Ser. No. 07/017,088 filed Feb. 20, 1987, abandoned, which was a continuation of Ser. No. 06/651,279 filed Sep. 17, 1984, now abandoned.

BACKGROUND OF THE INVENTION

1. Field of the Invention

This invention relates to an autoradiographic genescreening method.

2. Description of Prior Arts

In molecular biology which has been rapidly developed in recent years, it is essential to obtain genetic information on organisms so as to make the function of the organisms or the mechanism of replication clear. For this purpose, it is required to judge whether a gene having specific genetic information does exist in the tissues of organisms or in substances originating from the organisms or not, and to screen and recover the specific gene. This process is termed "gene-screening". Further, it is essential in genetic engineering that the existence of recombinant DNA is confirmed and the recombinant DNA is screened and recovered.

The gene-screening serves as an important means for identifying the corresponding gene in the genetic diagnosis of hereditary diseases. For example, rapid diagnosis for such a disease as cancer at molecular level is eagerly desired. It is also desired to establish a method for diagnosing a pregnant woman on whether a fetus in her body has inborn abnormality or not. It is significantly important that the diagnosis of these diseases can be made by detecting variance in the level of genes.

Accordingly, the detection or screening of genes having specific genetic information is of great value in the above-mentioned various fields. However, the ratio of the specific gene to the whole genomes is very low so that the practical detection or screening of the specific gene is very difficult.

As methods for screening genes, various attempts have been made. As typical methods, there can be mentioned: a chemical analysis method such as column chromatography or electrophoresis utilizing a difference in molecular weights of genes, chemical characteristics thereof, etc.; a biological method which comprises screening the specific genes by utilizing a difference in manifestation character against drug resistance, enzyme activity, etc.; and a probe method which utilizes the ability capable of forming a hybrid between complementary DNAs and RNAs (that is called "hybridization method").

Among these screening methods, the chemical analysis method is hardly employed in practice, because the amount of gene is very small and further the proportion of the specific gene to the whole genomes is very low so that it is very difficult to selectively detect or separate the specific gene. The biological method has a disadvantage in that manifestation of function related to the specific gene is indispensable to the method and the specific gene itself is not always active. As compared with these two methods, the probe method has advantages in that hybridization occurs very selectively and that the procedure is very simple.

As the typical gene-screening method utilizing a hybridization process according to the probe method, there can be mentioned the Southern blotting method. This method can be carried out in the following manner.

In the first place, a large amount of DNAs (or DNA fragments) containing the specific gene are resolved (or developed) on a medium, for example, by means of electrophoresis.

In the second place, double-stranded DNAs on the medium are denatured to form single-stranded DNAs. At least a portion of the denatured DNAs are then transferred to a transfer support (i.e., transfer medium) such as a nitrocellulose filter and fixed thereonto. A hybridization treatment is then carried out on the resulting transfer support.

In carrying out the hybridization treatment, DNA or RNA which is complementary to DNA containing the specific gene is radioactively labeled to prepare a probe. The radioactively labeled DNA or RNA is then hybridized with the denatured DNA on the transfer support. Thus, only a hybrid of DNA containing the specific gene with the radioactively labeled DNA or RNA is formed on the transfer support and it is at the same time radioactively labeled. Namely, the denatured DNA containing the specific gene is hybridized with the radioactively labeled DNA or RNA by heat treatment, and the renaturation of doublestranded DNA or the formation of a DNA-RNA hybrid takes place on the transfer support.

After the hybridization treatment is complete, the transfer support is subjected to autoradiography for detecting the DNA containing the specific gene. Further, after the DNA containing the specific gene is identified, only the DNA can be selectively isolated from the medium used for resolution.

Accordingly, through the above-stated gene-screening procedure (utilizing a hybridization process) according to the Southern blotting method (which is sometimes called Southern transfer method), DNA containing the specific gene can be detected and identified.

As another method for screening genes utilizing a hybridization process, there can be mentioned a screening method according to Northern blotting method.

In the Northern blotting mehod (which is sometimes called Northern transfer method), specimens are RNAs or RNA fragments and a hybridization procedure is carried out in a similar manner to that described above, using radioactively labeled DNA as a radioactively labeled probe.

The above-summerized gene-screening methods utilizing the Southern blotting method or Northern blotting method are described in more detail in the following texts.

METHOD IN ENZYMOLOGY, Vol. 68, pp. 152–176, pp. 220–242, edited by Ray Wu, ACADEMIC PRESS, New York, 1979.

PROTEIN, NUCLEIC ACID & ENZYME (in Japanese), Vol. 26, No. 4, pp. 584–590 (1981)

In carrying out the conventional autoradiography employed for the gene-screening, a radiographic film such as a high-speed X-ray film is combined in layers with a transfer support retaining a captured radioactively labeled probe for a given time so that the film is exposed to the radiation from the transfer support. A radiographic intensifying screen is generally employed to enhance the detection sensitivity of autoradiography.

Such autoradiography is described, for example, in the following text: Method in Biochemical Experiment, Vol. 6, Method in Tracer Experiment I, pp. 271-289, "8. Autoradiography" by Toru Sueyoshi & Akiyo Shigematsu (Tokyo Kagaku Dozin Ltd., 1977).

Therefore, the autoradiography is an important means for detecting the specific gene in the gene-screening method. Further, it can be said that the autoradiography is a very useful means, since the identification of the specific gene as well as the isolation and the purification of said gene can be done according to the obtained two-dimensional information on the location of said gene. Nevertheless, such useful autoradiography is not free from several drawbacks in the practical use when applied to the gene-screening method utilizing the hybridization mentioned above.

As described above, in the conventional autoradiography, a transfer support containing a radioactively labeled substance is brought into contact in layers with a radiographic film such as a high-speed X-ray film for a given time so that the film is exposed to the radiation and then a visible image indicating the position of the radioactive substance is obtained.

The primary drawback resides in that the exposure operation requires a long period of time. The exposure operation in the conventional autoradiographic screening is usually carried out for several days, and requires at least several tens of hours even when a radiographic intensifying screen is employed. This is because the amount of nucleic acid such as DNA fixed to the transfer support is small and the radioactively labeled substance (radioactively labeled probe) is generally a nucleic acid partially labeled with $^{32}P$, etc. so that intense radioactivity is not imparted thereto.

The second drawback resides in that the exposure operation should be carried out usually at a low temperature, for example, a temperature in the range of 0° C. to −80° C. This is because a latent image in silver salt of the film formed by exposure to a radiation or light emission, tends to fade at a relatively high temperature such as room temperature, and the so degraded latent image can be no longer developed to give a readable image. Further, the silver salt is easily fogged chemically through migration of deleterious ingredients from the hybridization-treated transfer support to the silver salt layer at such a high temperature. Another reason resides in that the silver salt forms a latent image with difficulty at a relatively high temperature such as room temperature even in the case of utilizing an intensifying screen, because the screen gives an emission of low intensity.

The third drawback resides in that the exposure ought to be carried out in a dry state to prevent the radiographic film from wetting and being fogged. Generally, the exposure is done after the transfer support is dried, or after the support is enclosed in a synthetic resin wrapping film, etc.

When the image obtained by the autoradiography is fogged as described above, the hydridized nucleic acid is hardly located on the obtained image and hence, the result of screening is made remarkably unfavorable.

For these reasons, the operation involved in the conventional autoradiography is complicated, whereby the gene-screening procedure is made complicated as a whole.

Other drawbacks of the conventional autoradiographic gene-screening method are given below.

The photosensitive silver salt of the radiographic film is readily influenced by physical irritation and the radiographic film easily produces fogging under application of physical pressure caused by the contact of the film with the hands of operators or the instrument in the exposure operation. Such unfavorable phenomenon also causes lowering in accuracy of the gene-screening. In order to avoid the occurrence of physical fogging on the radiographic film, high skill and caution must be taken in the handling of the film and hence, the screening operation is further complicated.

The exposure operation in the conventional autoradiographic gene-screening method is conducted over a long period of time as described above so that it is unavoidable that the radiations from natural origin and radioactive impurities incorporated in the transfer support in addition to the radioactively labeled substance take part in the exposure of the radiographic film. Thus, the accuracy of the locational information on the labeled substance is lowered. In order to eliminate such interference and to set appropriate exposure conditions, parallel experiments using control samples are generally carried out to find out proper exposure time, but such experiments have disadvantages in that the number of experiments is increased because such parallel experiments and preliminary experiments for ascertaining appropriate exposure time are involved and hence, the operation is made complicated and less economical as a whole.

The operation of collecting the specific gene is performed in such a manner that the medium carrying nucleic acids (sample) resolved thereon is aligned with the radiographic film on which the autoradiograph of the transfer support is visualized to allow the gene of nucleic acid corresponding to positive-signals indicating the presence of the radioactively labeled substance to be identified and collected. Therefore, if the visualized autoradiograph does not have a satisfactory image indicating locational information owing to the improper conditions for the exposure operation of the transfer support, the accuracy of the gene-screening is lowered. Otherwise, the screening becomes impossible in some cases and accordingly the number of the screening operation involved necessarily increases.

Another disadvantage encountered in the conventional screening method utilizing hybridization technique and exposure to high-speed X-ray film is the difference of the size between the autoradiographed image and the gel support medium used to resolve DNA fragments. This difference of size is caused by shrinking of a transfer support during the transfer and fixing procedure. Therefore, great care should be taken on the identification and collection process.

The gene-screening method utilizing Southern blotting method shows prominently high sensitivity. It is required to detect a single gene from DNAs of human genome in the diagnosis of hereditary disease, etc. in the case that this method is utilized. Accordingly, it is desired to keep the accuracy of the image of autoradiograph from being lowered by the above-described phenomena and to enhance the accuracy of the gene-screening.

SUMMARY OF THE INVENTION

The present inventors have made studies to eliminate the aforementioned disadvantageous features associated with the conventional autoradiographic gene-screening method, and discovered that the aforementioned disadvantages can be effectively eliminated or reduced by using a stimulable phosphor sheet having a phosphor layer containing a stimulable phosphor as a radiosensitive material in place of the radiographic film.

Accordingly, the present invention provides an autoradiographic gene-screening method employing a hybridization process, which comprises:

(1) a step of transferring at least a portion of nucleic acids, fragments thereof or derivatives thereof resolved on a medium onto a transfer support to fix them thereonto;

(2) a step of hybridizing the nucleic acids, fragments thereof or derivatives thereof fixed to said transfer support with radioactively labeled probes; and (3) a step of obtaining locational information on the radioactively labeled substances on said transfer support, which comprises placing said transfer support having been subjected to the hybridization and a stimulable phosphor sheet in layers for a given period of time to cause said sheet to absorb at least a portion of radiation energy emitted by the radioactively labeled substances on said transfer support, exciting said stimulable phosphor sheet with an electromagnetic wave to release the radiation energy stored in said sheet as stimulated emission, and detecting the stimulated emission.

Further, the present invention also provides a gene-screening method which comprises obtaining the locational information on the radioactively labeled substances on the transfer support by detecting the stimulated emission in the same manner as described above and recovering nucleic acids, fragments thereof or derivatives thereof on the medium according to the obtained locational information.

The term "locational information" of the radioactively labeled substances on the transfer support in the present invention refers to various information such as the location of the radioactively labeled substances or their aggregate on the transfer support, for example, information on the location and shape of the aggregate of the radioactively labeled substances on the transfer support and on the concentration, the distribution, etc. of said radioactively labeled substances or their aggregate. Such information can be obtained singly or in combination.

BRIEF DESCRIPTION OF DRAWINGS

FIG. 1 is a flow chart illustrating the gene-screening method of the present invention wherein:

Figure 1:
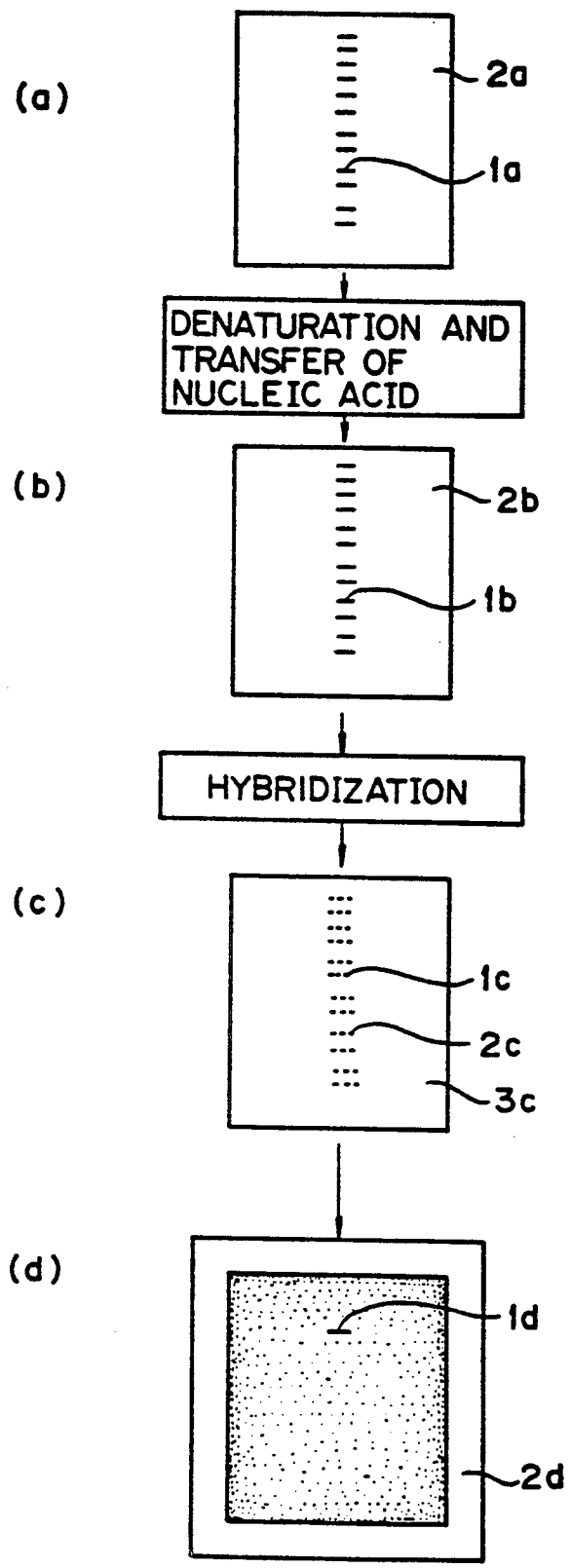

(a) shows a medium having DNA fragments resolved thereon in which 1a means DNA fragment and 2a means medium;

(b) shows a transfer support in which 1b means denatured DNA fragment and 2b means transfer support;

(c) shows a transfer support having hybrids formed thereon in which 1c means hybridized DNA fragment, 2c means unhybridized DNA fragment and 3c means transfer medium; and (d) shows a visualized autoradiograph in which 1d means black spot and 2d means radiographic film.

FIG. 2 schematically illustrates an embodiment of the read-out device for reading out the locational information on the radioactively labeled substances on a transfer support, which is recorded and stored in the stimulable phosphor sheet according to the present invention.

DETAILED DESCRIPTION OF THE INVENTION

The stimulable phosphor sheet used in the present invention is also called a radiation image storage panel and disclosed in, for example, U.S. Pat. No. 4,239,968 etc. and thus its general constitution is already known.

The stimulable phosphor sheet comprises a stimulable phosphor, in which said phosphor is capable of absorbing radiation energy having passed through an object or radiated from an object; and releasing the radiation energy stored therein as stimulated emission when said sheet is excited with an electromagnetic wave (stimulating rays) such as visible or infrared rays. The stimulated emission is photoelectrically detected and converted into electric signals which are then reproduced as a visible image on a display device such as CRT or on a recording medium such as a photographic film, or represented as locational information in the form of symbols and/or numerals. The stimulable phosphor sheet can be used repeatedly after erasing the radiation energy remaining therein which is done after being subjected to the readout operation. Therefore, the use of the stimulable phosphor sheet in the autoradiographic process according to the present invention is very advantageous.

According to the present invention, the stimulable phosphor sheet containing a stimulable phosphor is used in the autoradiographic gene-screening method for detecting the radioactively labeled substances captured on the transfer support and identifying the specific gene, in place of the radiographic film or a combination of the film with a radiographic intensifying screen used in the conventional autoradiography. By the use of the stimulable phosphor sheet, not only the exposure time is greatly shortened, but also the accuracy of the detection of the radioactively labeled substances is not lowered even when the exposure is carried out at an ambient temperature or at a temperature therearound. Therefore, the exposure operation previously taking many hours under chilling, is made simple and hence, the autoradiographic operation for detecting the radioactively labeled substances and identifying the specific gene can be greatly simplified.

Moreover, the exposure time in the autoradiography is greatly shortened so that time required for one screening operation can be shortened.

When the stimulable phosphor sheet is used as a radiosensitive material, there is not always required visualization for obtaining locational information on the radioactively labeled substances which is recorded and stored in the phosphor sheet and it is possible to obtain the locational information in any forms of an image, symbols and/or numerical values and a combination thereof by scanning the phosphor sheet with an electromagnetic wave such as a laser beam and reading out the locational information. Further, it is also possible to obtain the desired information in desired forms by further processing the obtained information with an appropriate electric means.

This means that the operation for judging the presence or absence of the specific gene based on the resulting locational information on the radioactively labeled substances and further the operation for recovering the specific gene based on said locational information can be made very easy and hence, the accuracy of screening is enhanced and its efficiency is improved.

Further, when the stimulable phosphor sheet is used as the radiosensitive material in the autoradiography, there occurs no problem of chemical and physical fog which is a nuisance in the use of the conventional radiographic film. Hence, the use of the stimulable phosphor sheet is very advantageous from the viewpoints of the improvement of the accuracy of screening and workability. Further, it is possible to readily eliminate or reduce the disadvantageous features associated with the conventional operation such as lowering in the accuracy caused by natural radioactivity or radioactivity of the impurities contained in the transfer support, through electrically processing the locational information stored in the stimulable phosphor sheet. Particularly, the gene-screening method utilizing the Southern blotting method is very sensitive so that it is very significant that by improving the accuracy of the resulting autoradiograph, the accuracy in the detection of the specific gene can be heightened and further the sensitivity of the detection can be enhanced.

The following illustrates the gene-screening method utilizing the Southern blotting method as an embodiment of the autoradiographic gene-screening method of the present invention.

FIG. 1 schematically illustrates an embodiment of the gene-screening method utilizing hybridization according to the present invention.

In the first place, a plurality of DNA fragments including a DNA fragment containing the specific gene are resolved by conducting electrophoresis on a gel support medium (FIG. 1-(a), 1a: DNA fragment, 2a: medium). It is desirable that the DNA fragments resolved on the support medium are dyed and a photograph thereof are taken to facilitate the detection and the identification of the specific gene in the subsequent stage.

In the second place, the DNA fragments resolved on the support medium are denatured by treating them with an alkaline solution to form single-stranded DNAs. According to the known Southern blotting method, at least a portion of the denatured DNA fragments are transferred onto a transfer support through a capillary action in such a manner that a nitrocellulose filter serving as the transfer support is placed on the gel support medium in layers, taking care to avoid trapping air beneath the filter and the stack is left to stand for 3 to 12 hours [FIG. 1-(b), 1b: denatured DNA fragment, 2b: transfer support]. Thus, the relation between the band pattern of the DNA fragments transferred to the transfer support and that of the DNA fragments resolved on the support medium is enantimorphous.

Examples of the transfer support which can be used for the transfer of DNA include a membrane filter made of nitrocellulose, a filter paper, etc.

The denatured DNA fragments on the transfer support is heat-treated to fix them thereonto.

Separately, a probe is prepared by radioactively labeled DNA or RNA which is complementary to DNA containing the specific gene. The probe can be prepared by labeling the terminal of RNA or DNA having a base sequence complementary to the specific DNA with a radioisotope such as $^{32}P$, etc.

Alternatively, the probe can be prepared by a nick translation method wherein one strand of an unlabeled double-stranded DNA having the same base sequence as that of the specific DNA is nicked by endonuclease, and nucleotides are sequentially removed from the nicked position in one strand and radioactively labeled nucleotides are introduced thereinto, using DNA polymerase I. According to this method, a probe having a high specific radioactivity can be obtained.

The denatured DNA fragments on the transfer support are then hybridized with the radioactively labeled probe by a heat treatment. The transfer support involving the radioactively labeled probe is warmed to renature the DNA to double-stranded DNA or to form DNA-RNA[1] hybrid. Since the denatured DNA on the transfer support is fixed, only the DNA fragment complementary to the DNA probe or the RNA probe is hybridized to capture the radioactively labeled probe and the unhybridized probe is then washed away with an appropriate solution. Thus, only the DNA fragment containing the specific gene forms a hybrid with the radioactively labeled DNA or RNA and hence, radioactive label is imparted thereto [FIG. 1-(c), 1c: hybridized DNA fragment, 2c: unhybridized DNA fragment, 3c: transfer support]. These DNA fragments can not be visually distinguished therebetween.

It is desirable that a mark is given on the transfer support with a radioactive ink so that the corresponding position can be aligned between the transfer support and the resulting autoradiograph.

In the case of forming the DNA-DNA hybrid, it is desirable to mask the transfer support with an appropriate solution as a pretreatment for hybridization in order to prevent the occurrence of noise in the autoradiographic process caused by non-specific adsorption of singlestranded DNA probe on the transfer support.

The transfer support on which the radioactively labeled substance is captured by the hybridization is then autoradiographed to detect and identify the DNA fragment containing the specific gene.

The characteristic feature of the present invention resides in the autoradiographic process for obtaining the locational information of the two-dimensionally distributed specific gene. In the autoradiographic process for obtaining such locational information, the exposure operation is conducted by placing the transfer support and the stimulable phosphor sheet together in layers for a given period of time to cause said phosphor sheet to absorb at least a portion of a radiation radiating from the radioactively labeled substances on the transfer support.

Generally, the transfer support is placed in close contact with the stimulable phosphor sheet during the exposure operation, but it is not always required to place the transfer support in close contact with the phosphor sheet and they may be placed adjacent to each other. The transfer support is not always required in a dry state, may be in a wet state and may be wrapped in a polyethylene sheet, etc. having such a thickness that does not interfere with transmittance of radiation from the probe.

The exposure time varies depending on the radiation intensity of the radioactively labeled substance contained in the transfer support, the amount of said substances, the sensitivity of the stimulable phosphor sheet and the distance between the transfer support and the stimulable phosphor sheet. The exposure operation must be carried out for a certain period of time, for example, for at least several seconds. In the present invention using the stimulable phosphor sheet as a radiosensitive material, however, the exposure time can be greatly shortened as compared with that required in the case where the conventional radiographic film is used. Further, the precise control of the exposure time is not particularly required, since the locational information on the radioactively labeled substances can be suitably processed in the subsequent read-out operation through applying various electrical processing thereto according to the intensity and distribution of energy stored in the phosphor sheet and the desired information form, for example, by setting the amplification of electric signals to a given value.

There is no specific limitation on the temperature in the exposure operation, and it is possible to carry out the exposure at an ambient temperature within the range of from 10° to 35° C. in the autoradiography according to the present invention. If desired, the exposure operation may be, of course, carried out at a low temperature of approximately 5° C. or lower as in the conventional autoradiography.

The stimulable phosphor sheet suitably employable in the aforementioned autoradiography is composed basically of a support and a phosphor layer comprising a binder and a stimulable phosphor dispersed therein, the phosphor layer being provided on said support. However, in the case that the phosphor layer is of a self-supporting type, the support is not always required.

The stimulable phosphor sheet of the above-described constitution can be prepared, for instance, by the following procedure.

In the first place, phosphor particles and a binder are added to an appropriate solvent (e.g., a lower alcohol, chlorine atom-containing hydrocarbon, ketone, ester, ether), and then they are well mixed to prepare a coating dispersion of the phosphor particles in the binder solution.

Examples of the binder include proteins such as gelatin and synthetic polymers such as polyvinyl acetate, nitrocellulose, polyurethane, polyvinyl alcohol, linear polyester and polyalkyl (meth)acrylate.

The ratio between the binder and the phosphor in the coating dispersion generally is within the range of from 1:8 to 1:40 (binder:phosphor, by weight).

The coating dispersion is then coated evenly on a support to form a coating layer, and the coating layer is gradually heated to dryness to prepare the phosphor layer on the support. The thickness of the phosphor layer generally ranges from 50 to 500 μm.

The support may be any one of supports made of various materials which have been known as supports of intensifying papers (i.e., intensifying screens) in the conventional radiography. Examples of the employable supports include films of plastic materials such as cellulose lose acetate and polyethylene terephthalate, metallic sheets such as aluminum foil, ordinary papers, baryta papers, and resin-coated papers.

On the surface of the support to receive the phosphor layer may be provided one or more of an adhesive layer, a light-reflecting layer, a light-absorbing layer, etc.

On the surface of the phosphor layer opposite to the surface to face the support, a transparent protective film may be provided to protect the phosphor layer from physical and chemical deterioration. Examples of the material of the protective film include cellulose acetate, polymethyl methacrylate, polyethylene terephthalate and polyethylene. The thickness of the transparent protective film generally ranges from 0.1 to 20 μm.

Moreover, the surface of the stimulable phosphor sheet may be treated, for instance, hydrophilically, if desired.

The stimulable phosphor contained in the stimulable phosphor sheet utilized in the present invention gives stimulated emission when excited with stimulating rays after exposure to a radiation. From the viewpoint of practical use, the stimulable phosphor is desired to give stimulated emission in the wavelength region of 300-500 nm when excited with stimulating rays in the wavelength region of 400-850 nm.

Examples of the stimulable phosphor employable in the radiation image storage panel of the present invention include:

SrS:Ce,Sm, SrS:Eu,Sm, $ThO_2$:Er, and $La_2O_2S$:Eu,Sm, as described in U.S. Pat. No. 3,859,527;

ZnS:Cu,Pb, $BaO \cdot xAl_2O_3$:Eu, in which x is a number satisfying the condition of $0.8 \leq x \leq 10$, and $M^{2+}O \cdot xSiO_2$:A, in which $M^{2+}$ is at least one divalent metal selected from the group consisting of Mg, Ca, Sr, Zn, Cd and Ba, A is at least one element selected from the group consisting of Ce, Tb, Eu, Tm, Pb, Tl, Bi and Mn, and x is a number satisfying the condition of $0.5 \leq x \leq 2.5$, as described in U.S. Pat. No. 4,326,078;

$(Ba_{1-x-y},Mg_x,Ca_y)FX:aEu^{2+}$, in which X is at least one element selected from the group consisting of Cl and Br, x and y are numbers satisfying the conditions of $0 < x+y \leq 0.6$, and $xy \neq 0$, and a is a number satisfying the and $xy \neq 0$, and a is a number satisfying the condition of $10^{-6} \leq a \leq 5 \times 10^{-2}$, as described in Japanese Patent Provisional Publication No. 55(1980)-12143;

LnOX:xA, in which Ln is at least one element selected from the group consisting of La, Y, Gd and Lu, X is at least one element selected from the group consisting of Cl and Br, A is at least one element selected from the group consisting of Ce and Tb, and x is a number satisfying the condition of $0 < x < 0.1$, as described in the U.S. Pat. No. 4,236,078;

$(Ba_{1-x},M^{II}_x)FX:yA$, in which $M^{II}$ is at least one divalent metal selected from the group consisting of Mg, Ca, Sr, Zn and Cd, X is at least one element selected from the group consisting of Cl, Br and I, A is at least one element selected from the group consisting of Eu, Tb, Ce, Tm, Dy, Pr, Ho, Nd, Yb and Er, and x and y are numbers satisfying the conditions of $0 \leq x \leq 0.6$ and $0 \leq y \leq 0.2$, respectively, as described in U.S. Pat. No. 4,239,968;

$M^{II}FX \cdot xA:yLn$, in which $M^{II}$ is at least one element selected from the group consisting of Ba, Ca, Sr, Mg, Zn and Cd; A is at least one compound selected from the group consisting of BeO, MgO, CaO, SrO, BaO, ZnO, $Al_2O_3$, $Y_2O_3$, $La_2O_3$, $In_2O_3$, $SiO_2$, $TiO_2$, $ZrO_2$, $GeO_2$, $SnO_2$, $Nb_2O_5$, $Ta_2O_5$ and $ThO_2$; Ln is at least one element selected from the group consisting of Eu, Tb, Ce, Tm, Dy, Pr, Ho, Nd, Yb, Er, Sm and Gd; X is at least one element selected from the group consisting of Cl, Br and I; and x and y are numbers satisfying the conditions of $5 \times 10^{-5} \leq x \leq 0.5$ and $0 < y \leq 0.2$, respectively, as described in Japanese Patent Provisional Publication No. 55(1980)-160078;

$(Ba_{1-x},M^{II}_x)F_2 \cdot aBaX_2:yEu,zA$, in which $M^{II}$ is at least one element selected from the group consisting of Be, Mg, Ca, Sr, Zn and Cd; X is at least one element selected from the group consisting of Cl, Br and I; A is at least one element selected from the group consisting of Zr and Sc; and a, x, y and z are numbers satisfying the conditions of $0.5 \leq a \leq 1.25$, $0 \leq x \leq 1$, $10^{-6} \leq y \leq 2 \times 10^{-1}$, and $0 < z \leq 10^{-2}$, respectively, as described in Japanese Patent Provisional Publication No. 56(1981)-116777;

$(Ba_{1-x},M^{II}_x)F_2 \cdot aBaX_2:yEu,zB$, in which $M^{II}$ is at least one element selected from the group consisting of Be, Mg, Ca, Sr, Zn and Cd; X is at least one element selected from the group consisting of Cl, Br and I; and a, x, y and z are numbers satisfying the conditions of $0.5 \leq a \leq 1.25$, $0 \leq x \leq 1$, $10^{-6} \leq y \leq 2 \times 10^{-1}$, and $0 < z \leq 2 \times 10^{-1}$, respectively, as described in Japanese Patent Provisional Publication No. 57(1982)-23673;

$(Ba_{1-x}, M^{II}{}_x)F_2 \cdot aBaX_2 : yEu, zA$, in which $M^{II}$ is at least one element selected from the group consisting of Be, Mg, Ca, Sr, Zn and Cd; X is at least one element selected from the group consisting of Cl, Br and I; A is at least one element selected from the group consisting of As and Si; and a, x, y and z are numbers satisfying the conditions of $0.5 \leq a \leq 1.25$, $0 \leq x \leq 1$, $10^{-6} \leq y \leq 2 \times 10^{-1}$, and $0 < z \leq 5 \times 10^{-1}$, respectively, as described in Japanese Patent Provisional Publication No. 57(1982)-23675;

$M^{III}OX : xCe$, in which $M^{III}$ is at least one trivalent metal selected from the group consisting of Pr, Nd, Pm, Sm, Eu, Tb, Dy, Ho, Er, Tm, Yb, and Bi; X is at least one element selected from the group consisting of Cl and Br; and x is a number satisfying the condition of $0 < x < 0.1$, as described in Japanese Patent Provisional Publication No. 58(1983)-69281;

$Ba_{1-x}M_{x/2}L_{x/2}FX : yEu^{2+}$, in which M is at least one alkali metal selected from the group consisting of Li, Na, K, Rb and Cs; L is at least one trivalent metal selected from the group consisting of Sc, Y, La, Ce, Pr, Nd, Pm, Sm, Gd, Tb, Dy, Ho, Er, Tm, Yb, Lu, Al, Ga, In and Tl; X is at least one halogen selected from the group consisting of Cl, Br and I; and x and y are numbers satisfying the conditions of $10^{-2} \leq x \leq 0.5$ and $0 < y \leq 0.1$, respectively, as described in U.S. patent application Ser. No. 497,805;

$BaFX \cdot xA : yEu^{2+}$, in which X is at least one halogen selected from the group consisting of Cl, Br and I; A is at least one fired product of a tetrafluoroboric acid compound; and x and y are numbers satisfying the conditions of $10^{-6} \leq x \leq 0.1$ and $0 < y \leq 0.1$, respectively, as described in U.S. patent application Ser. No. 520,215;

$BaFX \cdot xA : yEu^{2+}$, in which X is at least one halogen selected from the group consisting of Cl, Br and I; A is at least one fired product of a hexafluoro compound selected from the group consisting of monovalent and divalent metal salts of hexafluoro silicic acid, hexafluoro titanic acid and hexafluoro zirconic acid; and x and y are numbers satisfying the conditions of $10^{-6} \leq x \leq 0.1$ and $0 < y \leq 0.1$, respectively, as described in U.S. patent application Ser. No. 502,648;

$BaFX \cdot xNaX' : aEu^{2+}$, in which each of X and X' is at least one halogen selected from the group consisting of Cl, Br and I; and x and a are numbers satisfying the conditions of $0 < x \leq 2$ and $0 < a \leq 0.2$, respectively, as described in Japanese Patent Provisional Publication No. 59(1984)-56479;

$M^{II}FX \cdot xNaX' : yEu^{2+} \cdot zA$, in which $M^{II}$ is at least one alkaline earth metal selected from the group consisting of Ba, Sr and Ca; each of X and X' is at least one halogen selected from the group consisting of Cl, Br and I; A is at least one transition metal selected from the group consisting of V, Cr, Mn, Fe, Co and Ni; and x, y and z are numbers satisfying the conditions of $0 < x \leq 2$, $0 < y \leq 0.2$ and $0 < z \leq 10^{-2}$, respectively, as described in U.S. patent application Ser. No. 535,928; and $M^{II}FX \cdot aM^{I}X' \cdot bM'^{II}X''_2 \cdot cM^{III}X'''_3 \cdot xA : yEu^{2+}$, in which $M^{II}$ is at least one alkaline earth metal selected from the group consisting of Ba, Sr and Ca; $M^{I}$ is at least one alkali metal selected from the group consisting of Li, Na, K, Rb and Cs; $M'^{II}$ is at least one divalent metal selected from the group consisting of Be and Mg; $M^{III}$ is at least one trivalent metal selected from the group consisting of Al, Ga, In and Tl; A is at least one metal oxide; X is at least one halogen selected from the group consisting of Cl, Br and I; each of X', X'' and X''' is at least one halogen selected from the group consisting of F, Cl, Br and I; a, b and c are numbers satisfying the conditions of $0 \leq a \leq 2$, $0 \leq b \leq 10^{-2}$, $0 \leq c \leq 10^{-2}$ and $a + b + c \geq 10^{-6}$; and x and y are numbers satisfying the conditions of $0 < x \leq 0.5$ and $0 < y \leq 0.2$, respectively, as described in U.S. patent application Ser. No. 543,326.

The above-described stimulable phosphors are given by no means to restrict the stimulable phosphor employable in the present invention. Any other phosphor can be also employed, provided that the phosphor gives stimulated emission when excited with stimulating rays after exposure to a radiation.

Detailed description on the stimulable phosphor sheet and the exposing procedure employable in the present invention is given in Japanese Patent Application No. 57(1982)-193418 (U.S. patent application Ser. No. 549,417 and European Patent Application 83 110 984.8).

A method for reading out or detecting the locational information on the radioactivity labeled substances stored in the stimulable phosphor sheet will be described below briefly, referring to an embodiment of a read-out system shown in FIG. 2 of the accompanying drawings.

FIG. 2 schematically illustrates an embodiment of the read-out system comprising a preliminary read-out section 2 for preliminarily reading out the two-dimensional information on the location of the radioactively labeled substances stored (or recorded) in the stimulable phosphor sheet 1 (stimulable phosphor sheet may be hereinafter referred to as "phosphor sheet"), and a final read-out section 3 for finally reading out the desired locational information on the radioactively labeled substance stored in the phosphor sheet 1.

In the preliminary read-out section 2, the preliminary read-out operation is carried out in the following manner.

Laser beam 5 generated by a laser source 4 first passes through a filter 6 to cut off a light beam in the wavelength region corresponding to the wavelength region of stimulated emission to be emitted from the phosphor sheet 1 in response to stimulation with the laser beam 5. The laser beam 5 is subsequently deflected by a beam deflecter 7 such as a galvanometer mirror, and reflected by a plane reflecting mirror 8. The deflected beam then impinges upon the phosphor sheet 1. The laser source 4 used herein is so selected as to avoid overlapping of the wavelength region of the laser beam 5 with the main wavelength region of the stimulated emission to be emitted from the phosphor sheet 1.

The phosphor sheet 1 is transferred in the direction along the arrow 9 under the irradiation of the above-mentioned deflected laser beam. Therefore, the whole surface of the phosphor sheet 1 is subjected to the irradiation of the deflected laser beam. The power of the laser beam 5 employed in the preliminary read-out section is adjusted to be lower than the power of the laser beam to be employed in the final read-out section by controlling the output of the laser source 4, the beam diameter of the laser beam 5, the scanning speed of the laser beam 5, and the transferring speed of the phosphor sheet 1.

When irradiated with the above-mentioned laser beam, the phosphor sheet 1 gives stimulated emission having the emission intensity proportional to the radiation energy stored (or recorded) therein. The emission then enters into a light guiding sheet 10 for the preliminary readout. The light guiding sheet 10 has a linear edge face for receiving the emission, and the edge face is so positioned in the vicinity of the phosphor sheet as to correspond to the scanning line on the phosphor sheet 1. The exit of the light guiding sheet 10 is in the form of a ring and is connected to an light-receiving face of a light detector 11 such as a photomultiplier. The light guiding sheet 10 is made, for instance, by processing a sheet of a transparent thermoplastic resin such as a polyacrylic synthetic resin, and so constituted that the emission introduced from the linear edge face is transmitted to the exit under repeated total reflection within the sheet 10. The stimulated emission from the phosphor sheet 1 is guided in the interior of the light guiding sheet 10 to the exit, and received by the light detector 11.

On the light-receiving face of the light detector 11 is provided a filter which allows only the light of wavelength region of the stimulated emission to pass through and cuts off the light of the wavelength region of the stimulating rays (laser beam) so as to detect only the stimulated emission. The stimulated emission detected by the light detector 11 is converted to an electric signal, amplified in an amplifier 12 and transmitted to the output. The stored information output from the amplifier 12 is supplied to a control circuit 13 of the final read-out section 3. The control circuit 13 provides an amplification degree setting value a, a scale factor setting value b, and an image processing condition setting value c, for obtaining a well readable image having uniform concentration and contrast regardless of variation of the detected information.

The phosphor sheet 1 having been subjected to the preliminary read-out in the above-described manner is then transferred to the final read-out section 3.

In the final read-out section 3, the following read-out operation is performed.

The laser beam 15 generated by a laser source 14 for the final read-out passes through a filter 16 having the same function as that of the above-mentioned filter 6, and then the beam diameter is precisely adjusted in a beam expander 17. Subsequently, the laser beam is deflected by a beam deflector 18 such as a galvanometer mirror, and reflected by a plane reflection mirror 19. The deflected beam then impinges one-dimensionally upon the phosphor sheet 1. Between the beam deflector 18 and the plane reflection mirror 19 a fθ lens 20 is provided so that the beam speed is continuously kept constant while the deflected laser beam scans the phosphor sheet 1.

The phosphor sheet 1 is transferred in the direction along the arrow 21 under the irradiation with the above-mentioned deflected laser beam. Accordingly, the whole surface of the phosphor sheet is subjected to the irradiation in the same manner as in the preliminary read-out operation.

When irradiated with the above-mentioned laser beam, the phosphor sheet 1 gives the stimulated emission in proportion to the radiation energy stored therein in the same manner as in the preliminary read-out operation. The emission then enters into a light guiding sheet 22 for the final read-out. The light guiding sheet 22 for the final read-out is made of the same material and has the same constitution as the light guiding sheet 10 employed for the preliminary read-out. The stimulated emission received is guided in the interior of the light guiding sheet 22 up to the exit under repeated total reflection, and then received by a light detector 23. On the light-receiving face of the light detector 23 is provided a filter which allows only the light of wavelength region of the stimulated emission to pass through and cuts off the light of the wavelength region of the stimulating rays (laser beam) so as to detect only the stimulated emission.

The stimulated emission detected by the light detector 23 is converted to an electric signal, amplified to an electric signal adjusted to an appropriate level in an amplifier 24 according to the aforementioned amplification degree setting value a and transmitted to an A/D converter 25. The adjusted electric signal is then converted to a digital signal in the A/D converter 25 according to an appropriate scale factor defined by the scale factor setting value b, and then the digital signal is input into a signal processing circuit 26. In the signal processing circuit 26, the digital signal is processed according to the image processing condition setting value c for obtaining a well readable visible image having appropriate density and contrast regardless of variation of the detected information. If desired, the signal thus processed is then transmitted to a recording device (not shown) via a data preserving means such as a magnetic tape.

Various recording devices based on various systems can be employed for the above described purpose, for instance, a device for visualizing optically by scanning a photosensitive material with laser beam, etc., a display means for visualizing electrically on CRT, etc., a means for printing a radiation image displayed on CRT by means of video printer, and a means for visualizing on heat-sensitive recording material using thermic rays.

The recording device used in the present invention is not restricted to the visualizing devices such as mentioned above, and the two-dimensional information on the location of the radioactively labeled substance can be recorded, for example, in the form of numerals and/or symbols.

In the above description on the method for reading out the locational information on the radioactively labeled substances stored in the stimulable phosphor sheet, a read-out operation involving both the preliminary read-out operation and the final read-out operation has been given. However, the read-out operation employable in the present invention is not limited to the above-described embodiment. For instance, the preliminary read-out operation may be omitted if the content of the radioactive substances on the transfer support and an adequate exposure time for the transfer support is previously known.

Further, other suitable methods than the above-mentioned embodiments may be used for reading out the locational information of the radioactively labeled substances stored in the stimulable phosphor sheet.

The specific gene on the transfer support can be detected and identified from thus obtained two-dimensional information on the location of the radioactively labeled substances. For example, in the case that the autoradiograph of the transfer support is obtained as a visual image by using a radiographic film, only positions corresponding to the DNA fragments containing the specific gene are shown as black spots or blackened lines. Hence, it can be judged whether the DNA fragments contain the specific gene from the corresponding positions, density and size of the black spots appearing on the visual image or not, and the specific gene can be detected [FIG. 1-(d), 1d: black spot, 2d: radiographic film].

The specific gene on the transfer support can be identified by aligning this radiographic film with the photograph of the dyed gel support medium and comparing them with each other.

If desired, when the gel support medium is put upon the radiographic film having the visualized autoradiograph so as to make the positions agree with each other, the DNA fragments on the support medium which correspond to the black spots on the radiographic film are visually identified and the DNA fragments containing the specific gene can be collected. In the conventional method, even though the visualized autoradiograph on the radiographic film has the same size as that of nitrocellulose filter, the filter is shrunk during the course of the hybridization treatment so that care should be taken that the size of the resulting autoradiograph is somewhat smaller than that of the gel support medium. According to the present invention, however, the locational information can be easily processed electronically so that the size of the autoradiographed image can be adjusted to give the same size as that of the gel support medium. This makes identification of the electrophoresed spot or band of the specific DNA fragment much easier and therefore, the accuracy of screening can be increased.

The autoradiographic method of the present invention for detecting and identifying the DNA fragments which comprises obtaining the two-dimensional information on the location of the specific gene present on the transfer support is not limited to the above-described method which comprises employing the radiographic film having the visualized autoradiograph. For example, it is possible to detect and identify the DNA fragments containing the specific gene according to the digital value of the resulting numerals and/or symbols with which the locational information is expressed.

While the gene-screening method utilizing the Southern blotting method is described in the above, other methods than the Southern blotting method, such as the Northern blotting method can be also utilized in the present invention.

The Northern blotting method is one which employs a plurality of RNA fragments including RNA fragment containing the specific gene as a sample. In the gene-screening method of the present invention utilizing this method, RNA fragments resolved on a medium by means of electrophoresis are first transferred to a DMB paper. In a similar manner to that described above, RNA fragment containing the specific gene is hybridized with a radioactively labeled DNA probe, the RNA-DNA hybrid is autoradiographed, the specific gene is detected and identified according to the resulting two-dimensional information on the location of the radioactively labeled substances, and the RNA fragment containing the specific gene is recovered from the medium.

The gene-screening method of the present invention is not limited to that utilizing the Southern blotting method or Northern blotting method. Examples of the samples (or specimens) which can be used in the present invention include nucleic acids such as DNA and RNA; cleavage products obtained by cleaving the nucleic acids with a restriction enzyme, etc.; synthesized products obtained by synthesizing nucleic acids with a synthetic enzyme, etc.; fragments such as recombinant DNA fragments; nucleic acid derivatives such as methylated DNA or derivatives of their fragments.

Examples of the mediums on which the sample is resolved include support mediums for electrophoresis such as agarose gel, polyacrylamide gel, etc.; support mediums for thin layer chromatography such as silica gel, etc.; and support mediums for paper chromatography such as filter paper, etc.

Examples of the transfer supports to which the sample on the medium is transferred include DPT paper (or APT paper); DEAE paper; filters composed of nylon derivatives; filter paper, in addition to the aforementioned nitrocellulose paper and DBM paper (or ABM paper). As the methods for transferring the sample, there can be mentioned an electroblotting method (electrophoretical transfer) in addition to the aforementioned capillary method.

Examples of the radioactively labeled probes for use in the hybridization include radioactively labeled DNA, fragments thereof and derivatives thereof; and radioactively labeled RNA, fragments thereof and derivatives thereof. There is no limitation on the kind of the radioisotope employed as the radioactive label. Any other radioisotopic nucleus than $^{32}P$ can be employed, provided that the nucleus radiates radiation such as $\alpha$-rays, $\beta$-rays, $\gamma$-rays, proton beams, neutron beams or X-rays. Examples of the emplyable radioisotope include $^{14}C$, $^{35}S$, $^{3}H$, $^{125}I$ in addition to $^{32}P$.

As stated above, the gene-screening method of the present invention which comprises transferring at least a portion of nucleic acids, fragments thereof or derivatives thereof which are fractionated on an appropriate medium by a resolution procedure or the like to a suitable transfer support, radioactively labeling only the specific gene through a hybridization process and obtaining an autoradiograph thereof by using a stimulable phosphor sheet, is a method capable of simply detecting and identifying the specific gene with high accuracy. Further, the gene-screening method of the invention is a method capable of easily recovering nucleic acid containing the specific gene, fragment thereof or derivative thereof on a medium in a short time with high accuracy according to the two-dimentional information on the location of the radioactively labeled substances, said information being given by the autoradiograph.

The following examples illustrate an embodiment of the present invention. The stimulable phosphor sheet used in the following examples was prepared in the following manner.

Methyl ethyl ketone was added to a mixture of a particulate divalent europium activated barium fluorobromide (BaFBr: $Eu^{2+}$) stimulable phosphor and a linear polyester resin. Nitrocellulose (nitrification degree: 11.5%) was then added thereto to prepare a dispersion containing the phosphor particles dispersed therein. Tricresyl phosphate, n-butanol and methyl ethyl ketone were added to the dispersion and they were thoroughly stirred by means of a propeller mixer to prepare a coating dispersion having a viscosity of 25-35 poise at 25° C., in which the phosphor particles were uniformly dispersed and the mixing ratio of the binder to the phosphor was 1:25, by weight.

The coating dispersion was uniformly coated on the surface of a carbon black-containing polyethylene terephthalate sheet (support; 250 μm thick) placed horizontally on a glass plate by using a doctor blade. After the coating was complete, the support having a coating layer formed thereon was placed in a dryer and the temperature within the dryer was gradually elevated from 25° to 100° C. to dry the coating layer, thus forming a phosphor layer of 300 μm thick on the support.

A polyester adhesive was applied to one side of a transparent polyethylene terephthalate film (12 μm thick), and the film was bonded to the surface of the phosphor layer in such a manner that the adhesive layer faces the phosphor layer to form a protective film thereon. Thus, the stimulable phosphor sheet consisting essentially of a support, a phosphor layer and a protective film was prepared.

EXAMPLE 1

(1) Resolution by electrophoresis

DNA obtained from bacteriophage lambda (C1857S7) was cleaved by the use of restriction enzyme Hind-III by the known method to prepare a sample.

The mixture of DNA fragments (cleavage products of DNA) was charged on a 1.5% agrose gel (10 cm × 18 cm × 0.3 cm) and electrophoresed using 40 mM Tris-borate buffer solution (pH 8.2) to resolve the fragments on the gel.

The gel was soaked in the same buffer solution for electrophoresis containing ethidium bromide (0.5 μg/ml) to dye the DNA fragments. The gel was photographed under a UV lamp to obtain a fractionated image of the DNA fragments.

(2) Transfer from gel to nitrocellulose filter

The gel on which the DNA fragments were resolved was soaked in each of an aqueous solution of 1.5M sodium chloride and an aqueous solution of 0.5M sodium hydroxide for each 15 minutes. This operation was repeated twice, at each time a fresh solution being used, whereby double-stranded DNAs were denatured to single-stranded DNAs. The gel was then soaked in 1M tris-HCl buffer solution (pH 7.5). This operation was also repeated twice, at each time a fresh solution being used, whereby neutralization was effected.

According to the known Southern blotting method, the above gel was placed on a filter paper wetted with 20× SSC (1×SSC: a solution containing 0.15M sodium chloride and 0.15M sodium citrate, pH 7), and subsequently a nitrocellulose filter (HAWP; available from Millipore Corp.) wetted with 2×SSC was placed on the gel. Further, several sheets of dry filter papers were placed on the top of the nitrocellulose filter. While the filter paper under the gel was occasionally wetted with 20×SSC, the stack was left to stand for about five hours to allow the denatured fragments on the gel to be transferred to the nitrocellulose filter.

(3) Hybridization treatment

The nitrocellulose filter carrying the denatured DNA fragments transferred thereonto was soaked in 2×SSC for 20 minutes and heated in a vacuum dryer at 80° C. to fix the DNA fragments onto the filter.

The filter was steeped in Denhardt solution (3×SSC solution containing 0.02% bovine serum albumin, 0.02% polyvinyl pyrrolidone and 0.02% Ficoll) at 65° C. for 3 hours to effect the masking of the filter.

The fourth fragment (4.2 Kbp) of cleavage products of lambda DNA obtained by the use of restriction enzyme Hind-III was radioactively labeled with $^{32}P$ by the nick-translation method. 0.5 μg of the radioactively labeled probe (specific activity: $1 \times 10^8$ cpm/μg) and 150 μg of calf thymus DNA were dissolved in Denhardt solution. The above filter was soaked in 10 ml of the obtained Denhardt solution, followed by heating at 65° C. for 30 hours to effect the hybridization of the radioactively labeled probe with the fragment containing the specific gene.

The filter was washed by soaking it in a solution containing 2×SSPE (1×SSPE: solution containing 0.18M sodium chloride, 10 mM sodium phosphate and 1 mM EDTA, pH 7.7) and 0.1% SDS at 65° C. for 15 minutes. This washing operation was repeated twice, at each time a fresh solution being used. Further, the filter was washed by soaking it in a solution containing 0.1×SSPE and 1% SDS at 50° C. for 15 minutes. This washing operation was also repeated twice, at each time a fresh solution being used. The filter was then dried at room temperature.

(4) Detection and identification of gene by autoradiography.

The hybridized nitrocellulose filter and the stimulable phosphor sheet were placed in layers, introduced into a medical X-ray cassette for direct radiography in a lighted room, and kept for exposure at room temperature for 30 minutes. The stimulable phosphor sheet was then placed in the read-out device of FIG. 2 to read out the autoradiograph of the filter which was stored therein, whereby the two-dimensional information on the location of the radioactively labeled probe was obtained as digital values.

On the basis of the resulting digital information, a photographic film was exposed by using a laser scanning device and developed to obtain a visual image having the autoradiograph. The visual image had an image quality comparable with that of the image obtained through the procedure of Comparison Example 1.

According to the locational information, the fourth fragment of cleavage products of the lambda DNA by the use of Hind-III, namely the radioactively labeled probe, could be easily identified on the photograph which was previously taken after dyeing the DNA fragments on the gel with ethidium bromide.

COMPARISON EXAMPLE 1

In the procedure of Example 1-(4) for the autoradiographic detection and identification of gene, a medical radiographic film (RX: available from Fuji Photo Film Co., Ltd.) in combination with a fluorescent intensifying screen (High standard 3D: available from Fuji Photo Film Co., Ltd.) were used in place of the stimulable phospor sheet. A hybridized nitrocellulose filter, the radiographic film and the intensifying screen in this order were placed together in layers and placed in a cassette to expose the film at −80° C. for 15 hours. The radiographic film was developed to obtain an autoradiograph.

The resulting image had an image quality corresponding to that of the autoradiograph obtained in the form of a visual image on the photographic film in Example 1.

It has been confirmed from Example 1 and Comparison Example 1 that the gene-screening method of the present invention (Example 1) allows the specific gene to be detected and identified in a short time by a simple procedure as compared with the conventional screening method (Comparision Example 1). It has been also found that the specific gene can be screened and collected efficiently in a high purity according the present invention.

We claim:

1. In an autoradiographic gene-screening method employing a hybridization process comprising:

(1) a step of transferring nucleic acids or polynucleotide fragments thereof resolved on a medium onto a transfer support to fix them thereunto;

(2) a step of hybridizing the nucleic acids or polynucleotide fragments thereof fixed onto said transfer support with radioactively labeled probes; and (3) a step of obtaining locational information on radioactively labeled substances on said transfer support, which comprises placing said transfer support having been subjected to the hybridization on a radiosensitive material to absorb by the radiosensitive material radiation energy emitted by the radioactively labeled substances on the transfer support so as to obtain locational information of the radioactively labeled substances by way of the radiosensitive material;

the improvement comprising employing a stimulable phosphor sheet containing a stimulable phosphor as the radiosensitive material, where the locational information of the radioactively labeled substances is obtained by exciting said stimulable phosphor sheet with an electromagnetic wave to release the radiation energy stored in said sheet as stimulated emission and detecting the stimulated emission; and the improvement further comprising performing the procedure for placing the transfer support on a radiosensitive material at a temperature in the range of 10° to 35° C.

2. The autoradiographic gene-screening method as claimed in claim 1, wherein said gene-screening method is carried out by utilizing Southern blotting method, and said nucleic acids or fragments thereof are DNAs or DNA fragments.

3. The autoradiographic gene-screening method as claimed in claim 1, wherein said gene-screening method is carried out by Northern blotting method, and said nucleic acids or fragments thereof are RNAs or RNA fragments.

4. The autoradiographic gene-screening method as claimed in claim 1, wherein said excitation of the stimulable phosphor sheet with an electromagnetic wave in the step (3) is carried out by scanning said sheet with the electromagnetic wave.

5. The autoradiographic gene-screening method as claimed in claim 1, wherein said locational information on the radioactively labeled substances in the step (3) is obtained as an image.

6. The autoradiographic gene-screening method as claimed in claim 1, wherein said locational information on the radioactively labeled substances in the step (3) is obtained in the form of symbols and/or numerals.

7. The autoradiographic gene-screening method claimed in claim 10, wherein said stimulable phosphor sheet comprises a support, a phosphor layer comprising a stimulable phosphor dispersed in a binder and a protective layer.

8. In an autoradiographic gene-screening method employing a hybridization process comprising:

(1) a step of transferring nucleic acids or polynucleotide fragments thereof resolved on a medium onto a transfer support to fix them thereunto;

(2) a step of hybridizing the nucleic acid or polynucleotide fragments thereof fixed onto said transfer support with radioactively labeled probes; and (3) a step of obtaining locational information on radioactively labeled substances on said transfer support, which comprises placing said transfer support having been subjected to the hybridization on a radiosensitive material to absorb by the radiosensitive material radiation energy emitted by the radioactively labeled substances on the transfer support so as to obtain locational information of the radioactively labeled substances by way of the radiosensitive material; and (4) a step of recovering the nucleic acids or polynucleotide fragments thereof on the medium according to the obtained location information;

the improvement comprising employing a stimulable phosphor sheet containing a stimulable phosphor as the radiosensitive material, where the locational information of the radioactively labeled substances is obtained by exciting said stimulable phosphor sheet with an electromagnetic wave to release the radiation energy stored in said sheet as stimulated emission and detecting the stimulated emission; and the improvement further comprising performing the procedure for placing the transfer support on a radiosensitive material at a temperature in the range of 10° to 35° C.

* * * * *